US00PP10425P

United States Patent [19]

Danziger

[11] Patent Number: Plant 10,425

[45] Date of Patent: Jun. 2, 1998

[54] PETUNIA PLANT NAMED 'CASCHOP'

[75] Inventor: Gabriel Danziger, Nir Tzvi, Israel

[73] Assignee: Danziger - "Dan" Flower Farm, Post Beit Dagan, Israel

[21] Appl. No.: 657,444

[22] Filed: Jun. 3, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,889 | 9/1994 | Danziger | Plt./68.1 |
| P.P. 8,914 | 9/1994 | Danziger | Plt./68.1 |
| P.P. 8,915 | 9/1994 | Danziger | Plt./68.1 |
| P.P. 8,934 | 10/1994 | Danziger | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,408 | 12/1995 | Rother | Plt./68.1 |
| P.P. 9,556 | 5/1996 | Tachibana et al. | Plt./68.1 |
| P.P. 9,577 | 6/1996 | Suzuki et al. | Plt./68.1 |

*Primary Examiner*—James R. Feyrer
*Assistant Examiner*—Kent L. Bell

[57] ABSTRACT

The petunia cultivar 'Caschop' is particularly characterized by large flowers that are intensely purple; a trailing plant habit and a long growing season with vigorous growth and abundant flower production that continues under hot or mild winter conditions.

1 Drawing Sheet

The present invention comprises a new and distinct cultivar of petunia, known by the cultivar name 'Caschop'.

'Caschop' was originated from a hybridization made by the inventor in a controlled breeding program in Mishmar Hashiva, Israel in 1995. The female parent was a proprietary line designated CV 14 and the male parent was a proprietary line designated CV 111.

'Caschop' was discovered and selected as one flowering plant within the progeny of the stated cross by the inventior Gaby Danziger in May 1995 in a controlled environment in Mishmar Hashiva.

The first act of asexual reproduction of 'Caschop' was accomplished when vegetative cuttings were taken from the initial selection in June 1995 in a controlled environment in Mishmar Hashiva by a technician working under the supervision of the inventor. Horticultural examination of selected units was initiated in September 1995 and has demonstrated that the combination of characteristics as herein disclosed for 'Caschop' are firmly fixed and are retained through successive generations of asexual reproduction.

'Caschop' has not been observed under all possible environmental conditions. The phenotype may vary somewhat with variations in environment such as temperature, light intensity and day length, without any variations in genotype. The following observations, measurements and comparisons describe the plants grown in Mishmar Hashiva under greenhouse conditions which approximate those generally used in commercial practice.

The following traits have been repeatedly observed and are determined to be basic characteristics of 'Caschop' which in combination distinguish this petunia as a new and distinct cultivar:

1. Excellent garden performance under full sunlight and suitable for indoor usage.
2. Good weather tolerance including vigorous growth under hot climate conditions. The plant tolerates mild winter conditions and recovers well after heavy rain.
3. Vigorous growth with trailing dark green (R.H.S. 143A) foliage.
4. Large flowers having an intense purple (R.H.S. 74A) color. Flowers after plant established.
5. The plant exhibits a long garden season, maintaining growth and flowering from early spring until late winter.

6. Is not susceptible to common diseases of petunia.
7. Displays well in hanging baskets.

Of the many commercial cultivars known to the inventor, the most similar in comparison to 'Caschop' is the cultivar 'Purple'. In comparison to 'Purple', the cultivar 'Caschop' has better garden performance due to its vigorous growth and vibrant flower color. Unlike 'Purple', the cultivar 'Caschop' maintains flowering under moderate winter conditions.

The accompanying photographic drawing shows typical flower and foliage characteristics of 'Caschop', with the color being as true as possible with illustrations of this type.

Sheet 1 is a side view of a typical specimen of the variety 'Caschop' showing the abundant flowers of distinctive color and plant form.

In the following description color references are made to The Royal Horticultural Society Colour Chart. The color values were determined between 10:00–12:00 a.m. on Jan., 1996 under full sunlight at Mishmar Hashiva.

Classification:

*Botanical.*—Petunia hybrid.

*Commercial.*—Petunia cultivar 'Caschop'.

Plant:

*Growth habit.*—Trailing, vigorous, fast growing.

*Plant height.*—6–8 inches.

*Spreading area.*—30 inches.

*Blooming period.*—Throughout year.

Stem:

*Thickness.*2–3 mm.

*Color.*—Dark green (R.H.S. 137C) with purple (R.H.S. 77A) coloration during low temperatures.

*Pubescence.*—Yes.

*Branching.*—Free.

*Length of internode.*—10–20 mm.

Leaf:

*Arrangement on stem.*—Alternate.

*Shape.*—Ovate.

*Size.*—Length: 110 mm. Width: 49 mm.

*Thickness.*—0.2 mm.

*Color.*—Green (R.H.S. 143A).

*Pubescence.*—Yes.

Flower:

*Orientation at opening.*—Upright.

*Type.*—Single.

*Shape.*—The shape is regular with a corolla that is united and has a long straight tube.

*Diameter.*—65–75 mm.

*Color.*—Upper surface: dark purple (R.H.S. 74A)—dark eye (R.H.S. 79A) with veins extending toward corolla margin. Lower surface: dark purple (R.H.S. 74A).

*Peduncle.*—Length: 15–20 mm. Color: Green (R.H.S. 143A).

*Reproductive organs.*—Pistil: Number: 1. Color: Green (R.H.S. 138C). Stamens: Number: 5. Anther: Light purple (R.H.S. 98C). Filament: White-green (R.H.S. 138D).

Disease Resistance 'Caschop' is not susceptible to common diseases of petunia and is resistant to most leaf diseases.

I claim:

1. A new and distinct cultivar of petunia plant named 'Caschop' as herein shown and described.

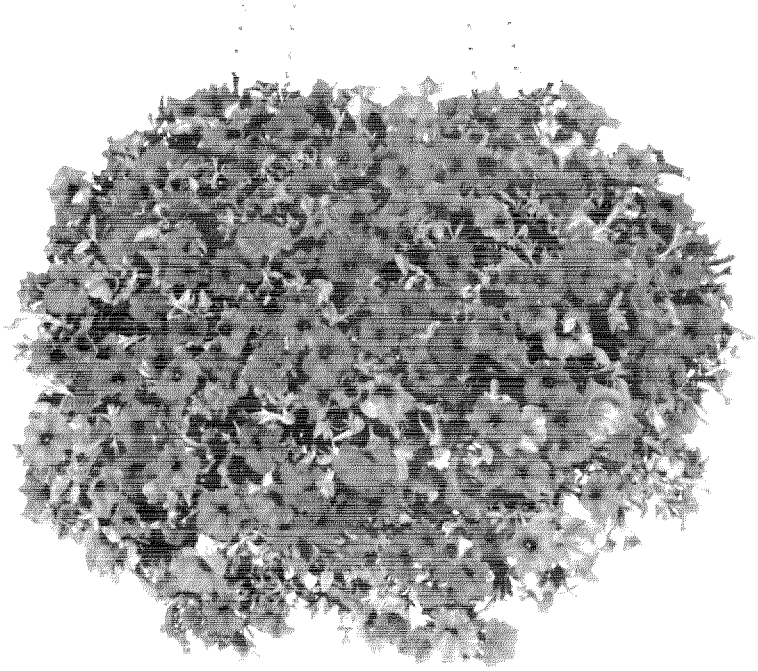

* * * * *